United States Patent [19]

Rysek

[11] 4,256,594
[45] Mar. 17, 1981

[54] HOT MELT METAL WORKING LUBRICANTS CONTAINING PHOSPHORUS-CONTAINING COMPOSITIONS

[75] Inventor: Joseph J. Rysek, Painesville, Ohio

[73] Assignee: The Lubrizol Corporation, Wickliffe, Ohio

[21] Appl. No.: 77,812

[22] Filed: Sep. 21, 1979

Related U.S. Application Data

[63] Continuation-in-part of Ser. No. 35,976, May 4, 1979, abandoned.

[51] Int. Cl.³ .............................................. C10M 1/46
[52] U.S. Cl. ..................... 252/49.9; 252/45; 252/46.6; 252/46.7; 252/49.8; 252/52 A; 260/951; 260/976; 428/416; 428/418; 428/419
[58] Field of Search ............... 252/46.6, 46.7, 49.8, 252/49.9, 52 A, 45; 260/951, 976; 428/416, 418, 419

[56] References Cited

U.S. PATENT DOCUMENTS

| | | | |
|---|---|---|---|
| 2,349,861 | 5/1944 | Hale | 252/45 |
| 2,621,159 | 12/1952 | Perry et al. | 252/58 X |
| 3,346,670 | 10/1967 | Papalos | 252/49.8 X |
| 3,420,921 | 1/1969 | Sorstokke | 260/976 |
| 3,496,104 | 2/1970 | Shimada et al. | 252/49.8 X |
| 3,526,596 | 9/1970 | Kress et al. | 252/52 A X |
| 3,553,131 | 1/1971 | Hepplewhite et al. | 252/49.9 X |
| 3,966,619 | 6/1976 | Smith et al. | 252/49.9 X |
| 4,116,872 | 9/1978 | Jahnke | 252/32.7 E |
| 4,118,331 | 10/1978 | Jahnke | 252/32.7 E |

FOREIGN PATENT DOCUMENTS

| | | | |
|---|---|---|---|
| 658479 | 2/1963 | Canada | 252/49.8 |
| 2205692 | 12/1972 | Fed. Rep. of Germany | 252/49.9 |

*Primary Examiner*—Andrew Metz
*Attorney, Agent, or Firm*—William H. Pittman; Daniel N. Hall; Raymond F. Keller

[57] ABSTRACT

Metal working operations, especially drawing, are facilitated by applying to the metal a composition which provides lubricity thereto, which melts between about 30° and about 150° C., and which contains a minor amount of a phosphorus-containing composition which may be prepared by the reaction of an alkoxylated alkyl phenol with a phosphorus trihalide, or, in combination with water, with a triaryl phosphite. The former reaction also produces, as a by-product, the corresponding halide. The phosphorus-containing compositions are especially useful in combination with a chlorinated wax. The preferred lubricant bases for the metal working lubricants comprise esters or polymers of epoxides or episulfides.

35 Claims, No Drawings

HOT MELT METAL WORKING LUBRICANTS CONTAINING PHOSPHORUS-CONTAINING COMPOSITIONS

This application is a continuation-in-part of copending application Ser. No. 035,976, filed May 4, 1979 now abandoned.

This invention relates to metal working operations. More particularly, it relates to compositions useful as lubricants and methods for lubricating metal during such operations, and to metal workpieces so lubricated.

Metal working operations, for example, rolling, forging, hot-pressing, blanking, bending, stamping, drawing, cutting, punching, spinning and the like generally employ a lubricant to facilitate the same. Lubricants greatly improve these operations in that they can reduce the power required for the operation, prevent sticking and decrease wear of dies, cutting bits and the like. In addition, they frequently provide rust inhibiting properties to the metal being treated.

Many of the lubricants applied for the above purposes are liquids. The equipment used for the application of such liquids is often expensive to maintain and inconvenient to use. In addition, a dry-off oven is usually required to remove the water or solvent carrier from the liquid composition, which also greatly adds to the capital costs and operating and maintenance expenses of the method. Difficulties are also often encountered in automatic feeding of metal blanks and otherwise handling the metal because the liquid compositions which are normally applied to the metal make it wet and slippery and consequently difficult to handle.

A principal object of the present invention, therefore, is to provide improved metal working compositions and methods.

A further object is to provide metal working lubricants which impart to the metal being worked a unique combination of properties including lubricity, corrosion resistance, extreme pressure properties and protection against wear of working parts.

Other objects will in part be obvious and will in part appear hereinafter.

According to this invention, the above objects are fulfilled by applying to the metal to be worked a composition which provides lubricity thereto, which melts between about 30° and about 150° C., and which contains a minor amount of a phosphorus-containing composition comprising at least one compound having the formula

$$[R^1-Ar^1(OR^2)_xO]_2POH$$

wherein:

Each $R^1$ is independently an aliphatic hydrocarbon-based radical having from about 4 to about 100 carbon atoms;

each $R^2$ is independently an ethylene, trimethylene, lower alkyl-substituted ethylene or lower alkyl-substituted trimethylene radical;

each $Ar^1$ is independently an aromatic radical; and each x is independently an integer from 1 to 15.

As used herein, the term "aliphatic hydrocarbon-based radical" denotes an aliphatic radical having a carbon atom directly attached to the remainder of the molecule and having predominantly hydrocarbon character within the context of this invention. Such radicals include the following:

(1) Hydrocarbon radicals; that is, aliphatic (e.g., alkyl or alkenyl) and aromatic-substituted aliphatic radicals, and the like. Such radicals are known to those skilled in the art; examples include butyl, octyl, decyl, dodecyl, eicosyl and triacontyl radicals (all isomers being included).

(2) Substituted hydrocarbon radicals; that is, radicals containing non-hydrocarbon substituents which, in the context of this invention, do not alter the predominantly hydrocarbon character of the radical. Those skilled in the art will be aware of suitable substituents (e.g., nitro, hydroxy, alkoxy, carbalkoxy).

(3) Hetero radicals; that is, radicals which, while predominantly hydrocarbon in character within the context of this invention, contain atoms other than carbon present in a chain or ring otherwise composed of carbon atoms. Suitable hetero atoms will be apparent to those skilled in the art and include, for example, nitrogen, oxygen and sulfur.

In general, no more than about three substituents or hetero atoms, and preferably no more than one, will be present for each 10 carbon atoms in the hydrocarbon-based radical.

Preferably, the hydrocarbon-based radicals present as $R^1$ in the phosphorus-containing compositions are free from acetylenic and usually also from ethylenic unsaturation and have from about 4 to about 50 carbon atoms, desirably from about 6 to about 25 carbon atoms. The radicals are usually hydrocarbon.

The aromatic radical $Ar^1$ may be a single-ring or fused-ring carbocyclic radical such as one derived from benzene, naphthalene, anthracene, phenanthrene, indene or the like, a similar radical containing substituents such as halo (especially chloro and bromo), nitro, hydroxy, carbalkoxy, sulfonic acid ester or the like, or a heterocyclic radical such as one derived from pyrrole, pyridine, indole or quinoline. Most often, however, $Ar^1$ is a single-ring carbocyclic aromatic radical and especially a hydrocarbon radical (that is, phenylene).

The radical $R^2$ is a divalent aliphatic radical having a straight chain of 2 or 3 carbon atoms. It is most often an ethylene or propylene radical, but may also be ethylene containing a lower alkyl substituent other than methyl, or a trimethylene or lower alkyl-substituted trimethylene radical (the term "lower" referring to radicals containing no more than 7 carbon atoms).

As is apparent from the formula, the compounds present in the phosphorus-containing composition may contain the same or different organic groups attached through oxygen to phosphorus, provided that each such group contains one or more alkoxy groups connecting the aromatic radical with the oxygen bonded to phosphorus. The integer x is usually 4 or less, but it may be higher, especially when balanced by an $R^1$ radical long enough to provide oil solubility.

It will be apparent that the above-identified phosphorus compounds are diesters of phosphorous acid in which the alcohol moieties are derived from certain oxyalkylated alkyl phenols and the like. Many of these oxyalkylated alkyl phenols are sold by Rohm & Haas Company under the designations "Triton X-15", "Triton X-35", etc. For the most part, $R^1$ in these "Triton" materials is an octyl radical, typically one derived from diisobutene.

The phosphorus-containing compositions may be prepared by a number of methods. One such method is by the reaction of at least one triaryl phosphite, preferably triphenyl phosphite, with water and at least one corresponding alcohol such as octylphenoxyethanol, the triaryl phosphite, alcohol and water being present in approximately 3:2:1 molar ratios. This reaction takes place under typical transesterification conditions and the product contains a substantial proportion of the phosphorous acid diester.

A second and preferred method for preparing the phosphorus-containing compositions is by the reaction of at least one corresponding alcohol with at least one phosphorus trihalide of the formula $PZ_3$ wherein Z is chlorine or bromine, preferably chlorine. This reaction is typically effected at temperatures between about 30° and about 150° C., by merely heating the alcohol with the phosphorus trihalide. Hydrogen halide is evolved during the reaction and may be removed by absorption in an alkaline material. If desired, the reaction may be carried out in the presence of a substantially inert, normally liquid organic diluent, although no such diluent is ordinarily required.

If the mole ratio of alcohol to phosphorus halide is approximately 3:1, the products of the reaction are one mole of the phosphorous acid diester and one mole of the corresponding halide. In a broad sense, therefore, the invention includes compositions comprising the previously defined phosphorus compound in combination with at least one halide of the formula

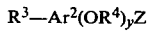
$$R^3—Ar^2(OR^4)_yZ$$

wherein $R^3$ is an aliphatic hydrocarbon-based radical having from about 4 to about 100 carbon atoms; $R^4$ is an ethylene, trimethylene, lower alkyl-substituted ethylene or lower alkyl-substituted trimethylene radical; $Ar^2$ is an aromatic radical; and y is an integer from 1 to 15. Under normal circumstances, as when the composition is prepared by the reaction of three moles of the alcohol with one mole of the phosphorus trihalide, $R^3$ will be identical with $R^1$, $R^4$ with $R^2$, $Ar^2$ with $Ar^1$ and y with x. When the mole ratio varies substantially from 3:1 (for example, when it is as high as 5:1 or as low as 1.5:1), the resulting composition may comprise more than an equimolar amount of the halide with respect to the phosphorus compound, or a mixture of the two compounds with excess alcohol, or a mixture of the phosphorous acid diester with monoesters and the like. Such mixtures are also contemplated for use as phosphorus-containing compositions although compositions comprising a substantially equimolar amount of the phosphorous acid diester and halide are preferred.

When an alcohol comprising a single molecular species is employed in either of the above-described reactions, the resulting phosphorus compound has two identical organic groups attached through oxygen to phosphorus. When a mixture of alcohols is employed, it will be apparent that the product may contain compounds in which the two organic groups are different.

The preparation of the phosphorus-containing compositions is illustrated by the following example. All parts are by weight.

EXAMPLE 1

A reaction vessel is fitted with a stirrer, condenser, addition funnel and temperature indicating means; the open end of the condenser is attached to a vessel containing aqueous sodium hydroxide solution. The reaction vessel is charged with 2055 parts (8.23 moles) of "Triton X-15", an octylphenoxyethanol. Phosphorus trichloride, 376 parts (2.74 moles), is charged to the addition funnel and added slowly with stirring, starting at a temperature of about 24° C. The temperature rises during the addition to about 59° C., whereupon the system is purged with nitrogen and heated slowly to 120° C. as phosphorus trichloride addition continues. When addition is complete, heating at 120° C. is continued for 15 minutes after which the mixture is vacuum stripped at 120° C. The product is the desired phosphite-chloride mixture containing 3.66% phosphorus and 4.31% chlorine, and having an acid number (bromophenol blue indicator) of 5.0.

The phosphorus-containing compositions function primarily to improve the antioxidant and extreme pressure properties of the lubricants of this invention. They can be employed in combination with any lubricant base which produces a lubricant melting between about 30° and about 150° C. to form a liquid which is capable of easy and efficient application to the metal surface. Such lubricant compositions (sometimes referred to hereinafter as "hot melt compositions") have the advantage that metals coated therewith are easier to handle under normal storage conditions than metals coated with previously known lubricants.

The principal necessary characteristic of the hot melt composition is its capability of providing lubricity to the metal surface. For this purpose, lubricity may be defined in many ways which are well known to those skilled in the art, and in terms of a number of test methods which, in one way or another, simulate metal working operations. For the purpose of this invention, a composition is deemed to provide lubricity to a metal workpiece if its use results in a deviation of 100 foot-pounds or less when tested by the following method:

A cold-rolled steel strip, $2''\times13\frac{1}{2}''$, is drawn between two dies in an Instron Universal Tester, Model TT-C. Prior to drawing, the edges of the strip are deburred and the strip is vapor degreased and wiped with a clean cloth. It is then coated uniformly with a drawing lubricant and mounted in the testing machine. The dies are tightened by means of a torque wrench set at 40 foot-pounds torque and the strip is pulled through the die for two inches at the rate of five inches per minute. The force or "load", in foot-pounds, required to pull the strip through the die, and the deviation from a uniform load, are recorded on a chart.

The hot melt composition melts in the range of about 30°–150° C., as previously indicated. Thus, it is solid at normal ambient temperature (e.g., about 20°–30° C.) and pressure. The preferred melting range is 35°–70° C., with 38°–55° C. being particularly desirable. When melted, the composition preferably forms a readily flowable liquid.

U.S. Pat. Nos. 4,116,872 and 4,191,658 are incorporated by reference herein for their disclosures of ester-based metal working lubricants of the hot melt type in which the compositions of this invention can be advantageously incorporated. The base lubricant in the ester-based hot melt compositions, broadly defined, is at least one ester of a carboxylic acid. Typical esters are those of acids having the formula $R^5(COOH)_m$ and organic hydroxy compounds having the formula $R^6(OH)_n$, wherein each of m and n is an integer from 1 to 3, $R^5$ is a hydrocarbon-based radical, and $R^6$ is a hydrocarbon-based or poly(oxyalkylene) radical. The hydrocarbon-based radicals are usually free from acetylenic and conjugated diene unsaturation and they preferably contain no more than one olefinic double bond.

The acid typically contains from about 4 to about 25 carbon atoms. The preferred acids are the aliphatic carboxylic acids, especially those in which $R^5$ is an alkyl or alkylene radical which may be branched or linear. Exemplary acids are propionic, butyric, stearic, oleic, benzoic, maleic, fumaric, succinic, adipic, glutaric, pimelic, sebacic, azelaic, suberic, phthalic, isophthalic, citric and trimellitic acids. The particularly preferred acids are the aliphatic monocarboxylic acids having from about 12 to about 25 carbon atoms and polycarboxylic, especially dicarboxylic, acids having from about 5 to about 10 carbon atoms.

The organic hydroxy compounds in which $R^6$ is a hydrocarbon-based radical typically contain at least about 10 and generally from about 10 to about 25 carbon atoms. Usually, n is 1 and $R^6$ is an alkyl radical which may be branched or linear. Exemplary organic hydroxy compounds are 1-butanol, 2-buten-1-ol, phenol, resorcinol, ethylene glycol, decanol, dodecanol, tetradecanol, stearyl alcohol, oleyl alcohol, eicosanol, and commercial mixtures of such alcohols. The preferred alcohols of this type are saturated aliphatic alcohols containing at least about 10 carbon atoms, especially $C_{14-20}$ alkanols (that is, saturated monohydroxy alcohols) and more especially predominantly straight-chain alkanols.

Another class of suitable organic hydroxy compounds consists of the polyalkylene glycols, especially the polyethylene and polypropylene glycols and preferably the former. The most desirable polyalkylene glycols are those containing from about 20 to about 50 oxyalkylene units. Such polyalkylene glycols are normally available as commercial mixtures such as the "Carbowax" polyethylene glycols sold by Union Carbide.

From the above descriptions of suitable acids and organic hydroxy compounds, it will be apparent that a wide variety of carboxylic acid esters are contemplated for use as hot melt lubricant bases. These include both neutral esters and acidic esters (e.g., monoesters of dicarboxylic acids), but neutral esters are preferably used. Both mono- and bis-esters of polyhydroxy compounds are contemplated.

The preferred esters are of two types. Type C comprises neutral esters of saturated aliphatic alcohols having at least about 10 and preferably up to about 25 carbon atoms and aliphatic polycarboxylic acids having from about 4 to about 20 carbon atoms. Especially preferred within Type C are esters of $C_{5-10}$ alkanedioic acids such as adipic, azelaic and sebacic acids and $C_{14-20}$ alkanols (particularly 1-alkanols) or commercial mixtures of such alkanols.

Type D comprises esters of $C_{12-25}$ aliphatic monocarboxylic (preferably alkanoic) acids such as myristic, palmitic and stearic acids, preferably stearic acid, and polyalkylene glycols (e.g., polyethylene or polypropylene glycol, the former being preferred) containing from about 20 to about 50 polyoxyalkylene units.

Mixtures consisting of about 5–95% by weight, and preferably about 5–20%, of esters of Type C, the balance being esters of Type D, are particularly desirable. Also useful are ester mixtures prepared by reacting a mixture of the above-described acids and alcohols.

Another genus of suitable hot melt lubricant bases comprises at least one polymer of at least one monoepoxide or monoepisulfide, said monoepoxide or monoepisulfide having the formula

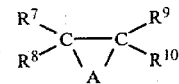

wherein $R^7$ is a substantially aliphatic hydrocarbon-based radical, each of $R^8$, $R^9$ and $R^{10}$ is individually hydrogen or a substantially aliphatic hydrocarbon-based radical, A is oxygen or sulfur, and the total number of aliphatic carbon atoms in $R^7$, $R^8$, $R^9$ and $R^{10}$ is from about 6 to about 23.

The term "substantially aliphatic" as used herein means that the radical comprises an aliphatic hydrocarbon-based chain which may, however, contain non-aliphatic substituents thereon. Such substituents include aromatic (e.g., phenyl and naphthyl), alicyclic (e.g., cyclohexyl and cyclopentyl) and heterocyclic (e.g., piperidyl and morpholino) groups. Such non-aliphatic groups will comprise no more than about 10% by weight of the substantially aliphatic hydrocarbon-based radical.

For the most part, $R^7$ and each of the other R radicals ($R^8$, $R^9$ and $R^{10}$) which are not hydrogen will comprise an aliphatic hydrocarbon radical and usually an alkyl radical. Monoepoxides wherein the epoxy group is in the $\alpha,\beta$-position (those in which $R^9$ and $R^{10}$ are hydrogen) are preferred and those in which $R^8$ is also hydrogen are especially preferred. Most desirable are epoxides of this type in which $R^7$ is an alkyl radical (especially a straight chain one) containing from about 10 to about 18 carbon atoms. Mixtures of such epoxides, including commercially available mixtures, are contemplated as suitable for the preparation of polymers for use in the invention.

Illustrative epoxides and episulfides whose polymers are useful as hot melt lubricant bases are 1-octene oxide, 2-octene oxide, 2,4,4-trimethyl-1-pentene oxide, 1-dodecene oxide, 1-hexadecene oxide, 1-eicosene oxide, butyl epoxystearate, and commercial mixtures of $C_{12-18}$ straight chain $\alpha$-olefin epoxides. Polymers of the corresponding episulfides are also useful.

The hot melt compositions of this type comprise at least one polymer of an epoxide or episulfide as described above. Copending allowed application Ser. No. 15,398, filed Feb. 26, 1979, and now U.S. Pat. No. 4,237,188 is incorporated by reference herein for its disclosure of suitable epoxide and episulfide polymers, which polymers include homopolymers of any single epoxide or episulfide and interpolymers containing units derived from more than one such epoxide, episulfide or mixture of epoxides with episulfides. They also include interpolymers of an epoxide or episulfide as described above with a lower or higher molecular weight epoxide or episulfide, usually a lower alkyl one such as ethylene oxide, propylene oxide or the corresponding sulfides. In general, such a copolymer containing units derived from epoxides or episulfides other than those described above will contain a major amount, usually above about 60% by weight, of units derived from epoxides or episulfides having the above formula. The number average molecular weight of the polymer is generally between about 500 and 10,000 as determined by gel permeation chromatography, and preferably between about 800 and about 2000.

The use of mixtures of two or more epoxide or episulfide polymers as a hot melt lubricant base is also contemplated. Specifically contemplated are compositions comprising a mixture of (C) at least one polymer as described hereinabove and (D) at least one polymer of ethylene oxide, propylene oxide or a mixture thereof. Such compositions will generally contain at least 50% by weight, and preferably about 70-95%, of component C. Component D usually also has a number average molecular weight between about 500 and about 10,000, as determined by gel permeation chromatography.

The epoxide or episulfide polymers are prepared by methods known in the art for the preparation of such polymers. A preferred method of preparation involves maintaining the epoxide or episulfide at a temperature up to about 60° C., preferably from about 30° to about 50° C., in the presence of a Lewis acid catalyst such as boron trifluoride or fluoboric acid. The following example is illustrative; all parts are by weight.

EXAMPLE 2

1-Hexadecene oxide (2000 parts) is cooled to 22° C. under nitrogen and 29 parts of a 50% aqueous solution of fluoboric acid is added slowly over 3 hours, with stirring. The reaction temperature is maintained at 36°-43° C. by intermittent cooling. The temperature is maintained at 40°-43° C. for one hour and is then increased to 50° C. as an additional 5 parts of fluoboric acid solution is added. The catalyst is neutralized by the addition of 11 parts of sodium carbonate and the product is filtered through a filter aid material to yield the desired epoxide polymer having a number average molecular weight of 1592 as determined by gel permeation chromatography.

Particularly desirable extreme pressure properties are imparted to metal working lubricants of this invention when the phosphorus-containing composition is incorporated therein in combination with a chlorinated wax. Combinations of chlorinated waxes (especially chlorinated paraffin waxes) and the phosphorus-containing composition are therefore contemplated as part of the invention. The chlorinated wax preferably has a molecular weight between about 350 and about 700 and contains about 30% to about 70% chlorine by weight, and the weight ratio of phosphorus-containing composition to chlorinated wax is typically between about 2.5:1 and about 0.5:1, preferably between about 1.5:1 and about 1:1.

In general, the lubricating compositions of this invention may contain from about 5 to about 30 parts by weight of the phosphorus-containing composition per 100 parts of lubricant, with an amount of chlorinated wax adequate to provide the weight ratios noted hereinabove. The lubricating compositions may additionally contain other additives. Especially preferred are carboxylic acids and derivatives thereof, which are typically present in the amount of 1 part by weight for about every 1.2 to 15 parts of phosphorus-containing composition. As used herein, the term "derivative" includes:

Anhydrides.

Esters, especially those prepared from lower alkyl monohydroxy or polyhydroxy compounds (e.g., methanol, ethanol, 1-butanol, n-hexanol, ethylene glycol, pentaerythritol) or epoxides (e.g., ethylene oxide, propylene oxide). The epoxide-derived compounds, as will be readily understood, are hydroxy esters.

Salts (neutral, acidic or basic) in which the cation is preferably one of a Group I or Group II metal, aluminum, tin, cobalt, lead, molybdenum, manganese, nickel or ammonium, including salts of the free acids and of their hydroxy esters. The lithium salts are preferred for their anti-rust properties.

Amides and amide-imide mixtures, especially those derived from aliphatic amines and more especially from lower aliphatic amines. The preferred amines are the alkylene polyamines, particularly ethylene polyamines.

Derivatives of the type described above may be obtained from the acids by known reactions or sequences of reactions.

The free acids, their lithium salts, and their anhydrides are most useful. Preferred are the aliphatic carboxylic acids (and derivatives thereof as defined hereinabove) containing from about 6 to about 75 and usually at least about 8 carbon atoms, and especially those in which the aliphatic radical is a hydrocarbon radical. These acids may be monocarboxylic or polycarboxylic, and are preferably monocarboxylic or dicarboxylic. Examples of suitable monocarboxylic acids are decanoic, lauric, palmitic, stearic, oleic and linoleic acids, with oleic acid being preferred. The preferred dicarboxylic acids and derivatives are the anhydrides of succinic acids having an aliphatic hydrocarbon-based substituent, such as those prepared by the reaction (more fully described hereinafter) of maleic acid or maleic anhydride with an aliphatic hydrocarbon-based compound containing at least about 6 carbon atoms, preferably from about 6 to about 75 and most often from about 10 to about 20 carbon atoms.

The hydrocarbon-based compound used for the preparation of the dicarboxylic acid or derivative thereof should be free from acetylenic unsaturation and substantially free from pendant groups containing more than about six aliphatic carbon atoms.

The preferred hydrocarbon-based compounds are those derived from substantially saturated petroleum fractions and olefin polymers, particularly oligomers of monoolefins (especially terminal monoolefins) having from 2 to about 10 carbon atoms. Thus, the hydrocarbon-based compound may be derived from a polymer of ethylene, propene, 1-butene, 2-butene, isobutene, 3-pentene, 1-octene or the like. Also useful are interpolymers of more than one olefin such as those illustrated above or of such olefins and other polymerizable olefinic substances such as styrene, chloroprene, isoprene, p-methylstyrene, piperylene and the like. In general, these interpolymers should contain at least about 80%, preferably at least about 96%, on a weight basis of units derived from the aliphatic monoolefins.

Other suitable hydrocarbon-based compounds are mixtures of saturated aliphatic hydrocarbons such as highly refined high molecular weight white oils or synthetic alkanes.

In some instances, the hydrocarbon-based compound should contain an activating polar radical to facilitate its reaction with the low molecular weight acid-producing compound. The preferred activating radicals are halogen atoms, especially chlorine, but other suitable radicals include sulfide, disulfide, nitro, mercaptan, ketone and aldehyde groups.

As previously noted, the preferred method for producing the dicarboxylic acid or derivative thereof is by the reaction of maleic acid or anhydride with the hydrocarbon-based compound, especially with a material such as a propene oligomer. This reaction involves merely heating the two reactants between about 100° and about 200° C. in the presence or absence of a substantially inert organic liquid diluent; an excess of a liquid reactant may also serve as the reaction medium. Other suitable reactions include oxidation with potassium permanganate, nitric acid or a similar oxidizing agent of a hydrocarbon-substituted 1,4-butanediol or the like; ozonolysis of a hydrocarbon-substituted 1,5-diene or the like; preparation of a bisorganometallic derivative of a hydrocarbon-substituted 1,2-dihalide or the like, followed by carbonation thereof with carbon dioxide; or preparation of a dinitrile followed by its hydrolysis. All of these reactions are well known in the art, as are the substituted succinic acids and derivatives thereof produced thereby.

Other additives which may be incorporated in the lubricants of this invention include:

Antioxidants, typically hindered phenols.

Surfactants, usually nonionic surfactants such as oxyalkylated phenols and the like.

Auxiliary extreme pressure agents such as sulfurized hydrocarbons, sulfurized esters, phosphorodithioic acid salts, etc.

Corrosion and water inhibiting agents, and auxiliary rust inhibiting agents.

Anti-stain agents such as salts of petrosulfonic acids, especially alkali metal salts and preferably sodium salts.

Friction modifying agents, of which the following are illustrative: $C_{10-20}$ fatty acid amides; $C_{10-20}$ alkyl amines, especially tallow amines, and ethoxylated derivatives thereof; salts of such amines with acids such as boric acid or phosphoric acid which have been partially esterified; $C_{10-20}$ alkyl-substituted imidazolines and similar nitrogen heterocycles; sulfurized derivatives of sperm oil and other fatty oils; basic barium or calcium salts of such oils or of amine-formaldehyde condensates, especially those derived from tallow amines such as described above; and gels derived from basic alkaline earth metal sulfonates.

Thixotropic or non-drip agents. These may include waxes and mixtures of aliphatic alcohols and hydrocarbons, especially those in about the $C_{20-34}$ range. Such alcohol-hydrocarbon mixtures are disclosed in U.S. Pat. No. 3,676,348, which is incorporated by reference herein for its disclosure thereof. The thixotropic agent need not be totally soluble in the remainder of the lubricant at ambient temperatures. A preferred thixotropic agent is a commercially available solid mixture of linear and branched chain $C_{20-30}$ alcohols and $C_{24-40}$ hydrocarbons melting at about 45°–50° C., sold by Ethyl Corporation under the trademark "Epal 20+".

Waxes and waxy polymers, such as crystalline (including microcrystalline) and non-crystalline hydrocarbon waxes, hydroxylated hydrocarbon waxes, petrolatum, and low molecular weight olefin polymers. Such waxes or polymers are typicaly present in amounts between about 0.25 and about 1.0 part by weight per part of lubricant base.

It is also within the scope of the invention to incorporate a small particle size, pigment-type particulate solid in the hot melt lubricant to increase lubricity at temperatures above the melting point thereof. Suitable in this respect are such pigments as rutile titanium dioxide, anatase titanium dioxide, zinc oxide, leaded zinc oxide, zinc sulfide, lead titanate, antimony oxide, zirconium oxide, white lead, basic lead silicate, lithopone, titanated lithopone, titanium-barium pigment, titanium-calcium pigment, titanium-magnesium pigment, calcium carbonate, gilders whiting talc, barytes, magnesium silicate, aluminum silicates, diatomaceous earth, china clay, Asbestine, silica and mica. Calcium carbonate is especially preferred. The amount of such pigment is typically from about 0.1 to about 0.2 part by weight per part of lubricant base.

It is preferred that the additives be soluble in the lubricant base, but the invention also contemplates the use of a substantially stable dispersion of the additives in the lubricant base.

In the following table are listed illustrative hot melt metal working lubricants of this invention.

| Ingredient Example | Parts by weight | | | | | |
|---|---|---|---|---|---|---|
| | A | B | C | D | E | F |
| Neutral adipic acid ester of commercial mixture of predominantly straight-chain $C_{16-18}$ 1-alkanols* | — | 72 | 66 | — | — | — |
| Stearic acid ester of "Carbowax 1540", a polyethylene glycol containing an average of 22–48 oxyethylene units per molecule | — | — | — | 73 | — | — |
| Ester mixture prepared from 0.75 equivalent of "Carbowax 1540", 0.25 equivalent of commercial mixture of predominantly straight-chain $C_{14-18}$ 1-alkanols*, 0.75 equivalent of stearic acid and 0.25 equivalent of adipic acid | — | — | — | — | 80 | 80 |
| Product of Example 2 | 80 | — | — | — | — | — |
| Product of Example 1 | 20 | 20 | 15 | 10 | 20 | 18 |
| Chlorinated paraffin wax, mol. wt. about 560, about 40% chlorine (by weight) | — | — | 10 | 8 | — | — |
| Tetrapropenyl succinic anhydride | — | 8 | 9 | — | — | — |
| Oleic acid | — | — | — | — | — | 2 |
| Dilithium salt of polybutenyl (mol. wt. about 1000) succinic acid | — | — | — | 9 | — | — |

*Available from Procter & Gamble

Any metal to be worked may be lubricated in accordance with this invention; examples are ferrous metals, aluminum, copper, magnesium, titanium, zinc and manganese as well as alloys thereof and alloys containing other elements such as silicon.

The lubricating compositions of this invention can be applied to the metal workpiece prior to or during the working operation in any suitable manner. They may be applied to the entire surface of the metal, or with any portion of that surface with which contact is desired. For example, the lubricant can be brushed or sprayed on the metal, or the metal can be immersed in a bath of the lubricant. In high speed metal forming operations spraying or immersion are preferred.

In a typical embodiment of the invention, a ferrous metal workpiece is coated with the lubricant prior to the working operation. For example, if the workpiece is to be drawn it may be coated with the lubricant before passage through the drawing die. It is also within the scope of the invention to apply the lubricant to the workpiece as it enters the die, or to apply it to the die itself whereupon it is transferred to the workpiece by contact. Thus, the method of this invention in a generic sense comprises any metal working operation wherein the workpiece has on its surface, during said operation, the above-described lubricant regardless of how applied.

The physical state of a hot melt metal working composition during application to the metal surface is not critical. Thus, it may be applied as a solid (as by rubbing) or as a liquid (as by brushing, spraying, dipping, flooding, roller coating, reverse roller coating or the like). For ease and convenience of application, it is preferably applied in the liquid state, and when this is done the metal may be subsequently cooled whereupon the hot metl composition solidifies, or it may be passed directly to the metal working operation while the composition is in the liquid state. One of the advantages of this invention, however, is that the hot melt composition solidifies to form a solid, non-blocking, non-slippery film on the metal workpiece, thus permitting convenient and safe material handling at reduced cost.

The surface temperature of the metal at the time the hot melt composition is applied may vary, for example, from normal ambient temperature to just below the decomposition temperature thereof. Factors which will influence or determine the temperature of the metal at the time the composition is applied include processes which the metal is subjected to prior or subsequent to application of the composition, the melting point of the composition, and the temperature thereof at the time application. Using the hot melt compositions described hereinabove, metal surface temperatures between about 20° and about 125° C. at the time of application have been found particularly useful. The temperature of the hot melt composition should preferably be higher than its melting temperature (preferably at least 10° C. higher and usually from about 20° to about 40° C. higher) at the time of application for ease of flow and uniform dispersion of the composition onto the metal and coverage thereby.

The melted hot melt composition may be applied to the metal in a minimum of space utilizing existing equipment such as coilers used in steel mills prior to coiling, and because it quickly solidifies at ambient temperatures and becomes dry, non-blocking and relatively non-slippery, standard handling equipment such as lifting and feeding rollers, stackers and so on may also be used. The use of the hot melt composition also eliminates the need for a dry-off oven since there is no water or solvent to remove.

What is claimed is:

1. A composition which melts between about 30° and about 150° C. and which provides lubricity to metal surfaces, said composition comprising a major amount of at least one ester or of a polymer of at least one monoepoxide, monoepisulfide or mixture thereof and containing a minor amount sufficient to furnish antioxidant and extreme pressure properties of a phosphorus-containing composition comprising at least one compound having the formula $$(R'-AR'OR^2O)_2POH$$

wherein:
Each $R^1$ is independently an aliphatic hydrocarbon-based radical having from about 4 to about 100 carbon atoms;
each $R^2$ is independently an ethylene, trimethylene, lower alkyl-substituted ethylene or lower alkyl-substituted trimethylene radical; and
each $Ar^1$ is independently an aromatic radical.

2. A composition according to claim 1 which melts between about 35° and about 70° C.

3. A composition according to claim 2 wherein $R^1$ is a hydrocarbon radical having from about 4 to about 25 carbon atoms, $R^2$ is ethylene or propylene, and $Ar^1$ is a single-ring carbocyclic radical.

4. A composition according to claim 3 wherein $Ar^1$ is a phenylene radical.

5. A composition according to claim 4 wherein $R^2$ is ethylene.

6. A composition according to claim 5 wherein $R^1$ is an octyl radical.

7. A composition according to claim 2 which also includes at least one compound of the formula $$[R^3-Ar^2(OR^4)_yZ] \quad R^3-Ar^2OR^4Z$$

wherein:
$R^3$ is an aliphatic hydrocarbon-based radical having from about 4 to about 100 carbon atoms;
$R^4$ is an ethylene, trimethylene, lower alkyl-substituted ethylene or lower alkyl-substituted trimethylene radical;
$Ar^2$ is an aromatic radical; and
$Z$ is chlorine or bromine.

8. A composition according to claim 7 wherein $R^3$ is identical with $R^1$, $Ar^2$ is identical with $Ar^1$, $R^4$ is identical with $R^2$, and $Z$ is chlorine.

9. A composition according to claim 8 wherein $R^1$ is a hydrocarbon radical having from about 4 to about 25 carbon atoms, $R^2$ is ethylene or propylene, and $Ar^1$ is a single-ring carbocyclic radical.

10. A composition according to claim 9 wherein $Ar^1$ is a phenylene radical.

11. A composition according to claim 10 wherein $R^2$ is ethylene.

12. A composition according to claim 11 wherein $R^1$ is an octyl radical.

13. A composition which melts between about 30° and about 150° C. and which provides lubricity to metal surfaces, said composition comprising a major amount of at least one ester or of a polymer of at least one monoepoxide, monoepisulfide or mixture thereof and containing a minor amount sufficient to furnish antioxidant and extreme pressure properties of a phosphorus-containing composition prepared by reacting at least one alcohol of the formula $R^1-Ar^1OR^2OH$ with at least one phosphorus halide of the formula $PZ_3$, wherein:
$R^1$ is an aliphatic hydrocarbon-based radical having from about 4 to about 100 carbon atoms;
$R^2$ is an ethylene, trimethylene, lower alkyl-substituted ethylene or lower alkyl-substituted trimethylene radical;
$Ar^1$ is an aromatic radical; and
$Z$ is chlorine or bromine.

14. A composition according to claim 13 which melts between about 35° and about 70° C.

15. A composition according to claim 14 wherein $R^1$ is a hydrocarbon radical having from about 4 to about 25 carbon atoms, $R^2$ is ethylene or propylene, $Ar^1$ is a single-ring carbocyclic radical, and $Z$ is chlorine.

16. A composition according to claim 15 wherein $Ar^1$ is a phenylene radical.

17. A composition according to claim 16 wherein $R^2$ is ethylene.

18. A composition according to claim 17 wherein $R^1$ is an octyl radical.

19. A composition according to claim 1, 6, 7, 8, 12, 13, or 18 which additionally contains at least one carboxylic acid or derivative thereof.

20. A composition according to claim 19 wherein the carboxylic acid is a monocarboxylic or dicarboxylic acid containing from about 6 to about 75 carbon atoms.

21. A composition according to claim 20 wherein the carboxylic acid is oleic acid.

22. A composition according to claim 1, 6, 7, 8, 12, 13, or 18 which additionally contains a minor amount of a chlorinated wax.

23. A composition according to claim 22 which additionally contains at least one carboxylic acid or derivative thereof.

24. A composition according to claim 23 wherein the carboxylic acid is a monocarboxylic or dicarboxylic acid containing from about 6 to about 75 carbon atoms.

25. A composition according to claim 24 wherein the carboxylic acid is oleic acid.

26. A method for lubricating metal during working thereof which comprises applying to said metal a lubricating composition according to claim 1, 6, 7, 8, 12, 13, or 18.

27. A method for lubricating metal during working thereof which comprises applying to said metal a lubricating composition according to claim 19.

28. A method for lubricating metal during working thereof which comprises applying to said metal a lubricating composition according to claim 20.

29. A method for lubricating metal during working thereof which comprises applying to said metal a lubricating composition according to claim 21.

30. A method for lubricating metal during working thereof which comprises applying to said metal a lubricating composition according to claim 22.

31. A metal workpiece having on its surface a film of a lubricating composition according to claim 1, 6, 7, 8, 12, 13, or 18.

32. A metal workpiece having on its surface a film of a lubricating composition according to claim 19.

33. A metal workpiece having on its surface a film of a lubricating composition according to claim 20.

34. A metal workpiece having on its surface a film of a lubricating composition according to claim 21.

35. A metal workpiece having on its surface a film of a lubricating composition according to claim 22.

* * * * *